United States Patent [19]

Uhlemann

[11] Patent Number: 4,825,874
[45] Date of Patent: May 2, 1989

[54] CARDIAC DIAGNOSIS INSTRUMENT

[76] Inventor: Hans J. Uhlemann, Elper Strasse 186, Herten, Fed. Rep. of Germany, 4352

[21] Appl. No.: 99,739

[22] Filed: Sep. 22, 1987

[30] Foreign Application Priority Data

Oct. 17, 1986 [DE] Fed. Rep. of Germany ....... 3635346

[51] Int. Cl.⁴ .............................................. A61B 5/04
[52] U.S. Cl. ................................... 128/710; 128/696; 128/706
[58] Field of Search ............... 128/696, 690, 710, 706, 128/687, 689

[56] References Cited

U.S. PATENT DOCUMENTS

| | | | |
|---|---|---|---|
| 3,858,576 | 1/1975 | Dehnert et al. | 128/712 |
| 4,350,164 | 9/1982 | Allain, Jr. | 128/639 |
| 4,596,256 | 6/1986 | Ascher et al. | 128/710 |
| 4,606,352 | 8/1986 | Geddes et al. | 128/712 |
| 4,686,998 | 8/1987 | Robbins | 128/696 |

FOREIGN PATENT DOCUMENTS

| | | | |
|---|---|---|---|
| 250557 | 11/1966 | Austria | 128/710 |
| 0027974 | 5/1981 | European Pat. Off. | 128/693 |
| 0170448 | 2/1986 | European Pat. Off. | 128/710 |
| 0178990 | 4/1986 | European Pat. Off. | 128/710 |
| 0207678 | 1/1987 | European Pat. Off. | 128/637 |
| 2646866 | 10/1977 | Fed. Rep. of Germany | 128/710 |
| 2928588 | 7/1979 | Fed. Rep. of Germany | 128/689 |
| 2915912 | 11/1980 | Fed. Rep. of Germany | 128/689 |
| 3409094 | 9/1985 | Fed. Rep. of Germany | 128/710 |
| 3407775 | 10/1985 | Fed. Rep. of Germany | 128/687 |
| 1571024 | 6/1969 | France | 128/693 |
| 56-67342 | 5/1981 | Japan | 128/693 |
| 57-8418 | 1/1982 | Japan | 128/710 |
| 2142727 | 1/1985 | United Kingdom | 128/710 |
| 2181554 | 4/1987 | United Kingdom | 128/710 |

OTHER PUBLICATIONS

Biosig Inc., "Inta-Pulse", 4-3-79, Montreal, Canada.

Primary Examiner—Francis Jaworski
Assistant Examiner—George Manuel
Attorney, Agent, or Firm—Sixbey, Friedman, Leedom & Ferguson

[57] ABSTRACT

According to the present invention there is provided a cardiac diagnosis instrument including an elongated housing, diagnosis electronics accommodated within the housing and two pick-up electrodes mounted on one long side of the housing close to the front and rear ends of the instrument and electrically connected to the diagnosis electronics, a voltage source within the housing, a flat thin graphic display unit which extends along one side for a substantial part of the length of the housing on the opposite side to that on which the pick-up electrodes are located, an on-off switch, said graphic display unit and said on-off switch being electrically connected to the diagnosis electronics, said diagnosis electronics including evaluation electronics and actuation electronics for the graphic display unit, said housing having a tubular shape somewhat like that of a fountain pen, and by placing the housing on a region of the body of a patient, the pick-up electrodes may be pressed into contact with the skin of the patient and thus the frequency of the heart beat, an electrocardiogram (ECG), the QRS complex of an ECG, an electroencephalogram (EEG) or the like may be investigated through the medium of the pick-up electrodes. Preferably one of the pick-up electrodes is in the form of a holding clip starting from one end of the housing.

11 Claims, 1 Drawing Sheet

CARDIAC DIAGNOSIS INSTRUMENT

The invention relates to a cardiac diagnosis instrument.

The known cardiac diagnosis instrument upon which this present invention is based (EP-Al No. 0 178 990) is especially suitable for use in emergencies and is independent of the location. In an emergency, the cardiac diagnosis instrument with its pick-up electrodes can be placed directly in contact with a region of the patient's body. The housing of this cardiac diagnosis instrument has a rectangular, plate-shaped configuration and the pick-up electrodes are situated on the underside of the housing and the graphic display unit or appropriate display screen as well as various other adjustment elements and optical and acoustic display elements are located on the opposite upper side of the housing. In the case of this cardiac diagnosis instrument, the resolution of the graphic display unit is adjustable. Naturally it is necessary to provide a reference display also which can be set either on the null line of the ECG or else in a free region of the graphic display unit. It is particularly expedient that the ECG displayed on the graphic display unit of this cardiac diagnosis unit can be selectively retained, meaning that the display can be frozen at a desired stage. This is achieved by actuation of one of the adjustment elements on the upper side of the housing while the instrument is still in contact with the patient's body. With the use of a further adjustment element, it is possible to erase a frozen display from the screen. Thus the cardiac diagnosis instrument may be removed from the patient's body after the display has been frozen and taken to a situation where it is more readily accessible and where the illumination is better for viewing the display of the ECG on the graphic display unit. In addition, an electric terminal is provided on the housing for attachment of a transmission cable.

The already-known cardiac diagnosis instrument which has been referred to is, however, not optimally suitable for wide distribution to all doctors, because the plate-shaped housing with relatively large surface area is rather voluminous and therefore takes up too much room in a doctor's bag or the like. The result is that this cardiac diagnosis instrument would not normally be carried around by a general practitioner when making house visits to patients.

Furthermore, an emergency diagnosis instrument is also known (U.S. Pat. No. 4,350,164) which can be carried around in a doctor's bag or in the pocket in his jacket without any inconvenience, because the housing has a tubular shape. However, this cardiac diagnosis instrument only gives the minimal amount of diagnostic information, namely the frequency of the heart beat by way of a blocking indicator light. Only with considerable additional structural modification, and by sacrifice of a simple and robust construction, is it possible to arrive at the situation where the distance between the pick-up electrodes which are concentrated on the end surface of the housing is sufficiently great. It is precisely this distance which is a fundamental prerequisite for arriving at a comprehensive and dependable diagnostic opinion. This cardiac diagnosis instrument is therefore not to be compared, with regard to its diagnostic capability, to the cardiac diagnosis instrument referred to initially and from which the present invention has been developed.

The problem to be solved by the present invention is how to configure the known cardiac diagnosis instrument in such a manner, with the retention of its diagnostic capability, that it can be conveniently carried around by a doctor in his doctor's bag or in the pocket of this jacket.

According to the present invention there is provided a cardiac diagnosis instrument including an elongated housing, diagnosis electronics accommodated within the housing and two pick-up electrodes mounted on one long side of the housing close to the front and rear ends of the instrument and electrically connected to the diagnosis electronics, a voltage source within the housing, a flat thin graphic display unit which extends along one side for a substantial part of the length of the housing on the opposite side to that on which the pick-up electrodes are located, an on-off switch, said graphic display unit and said on-off switch being electrically connected to the diagnosis electronics, said diagnosis electronics including evaluation electronics and actuation electronics for the graphic display unit, said housing having a tubular shape somewhat like that of a fountain pen, and by placing the housing on a region of the body of a patient, the pick-up electrodes may be pressed into contact with the skin of the patient and thus the frequency of the heart beat, an electrocardiogram (ECG), the QRS complex of an ECG, an electroencephalogram (EEG) or the like may be investigated through the medium of the pick-up electrodes. Preferably one of the pick-up electrodes is in the form of a holding clip starting from one end of the housing.

It has been found, in accordance with the invention, that an elongated graphic display unit may be mounted on a tubular housing without any difficulty. In addition, it was found that the arrangement of the pick-up electrodes on one of the long sides of the housing close to either the front or rear end of a housing may be retained even with a tubular housing so that a desired long distance between the electrodes can be ensured. Lastly, it has been found that a tubular housing, having a shape somewhat like that of a fountain pen, have a particularly expedient holding clip which, in the usual manner, starts from one end of the housing and which can act at the same time as one of the pick-up electrodes. Because of this ingenious configuration of the cardiac diagnosis instrument in accordance with the invention, it is quite convenient for it to be carried around all the time by all doctors without any difficulty. The cardiac diagnosis instrument can be carried around in the doctor's bag or even in the pocket of the doctor's jacket in a substantially similar fashion to an ordinary fountain pen or the like. In case that a holding clip is not provided for or that it is not convenient to have the holding clip acting as one of the pick-up electrodes, both pick-up electrodes may be formed on the housing directly.

There are a great number of possibilities for the development and improvement of the cardiac diagnosis instrument, for which purpose attention is drawn on the hand to the claims and, on the other hand, to the discussions of preferred embodiments of the invention which follow with reference to the accompanying drawings.

Figure 1:
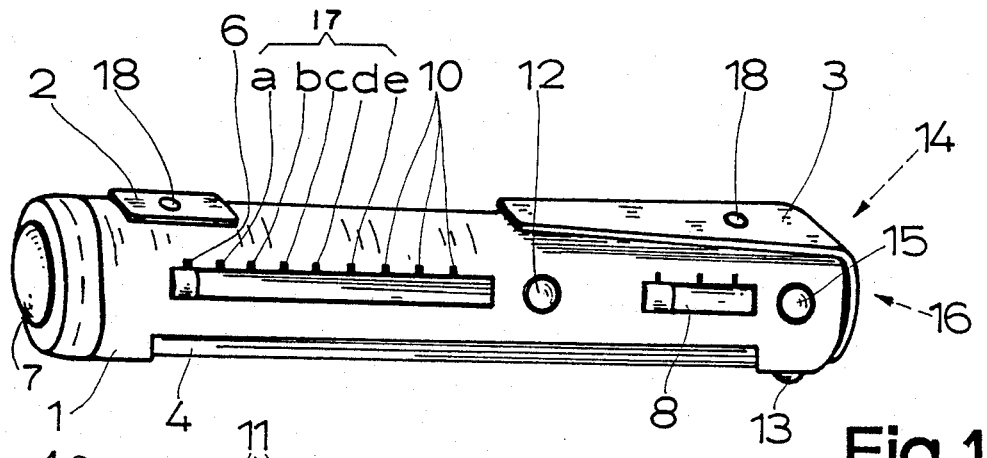
FIG. 1 is a perspective view of a first embodiment of a cardiac diagnosis instrument.

The first embodiment depicted in FIG. 1 is a fully integrated cardia diagnosis instrument having a housing 1 and diagnosis electronics (not shown) accommodated within the housing 1. Two pick-up electrodes 2, 3 are mounted on the outside of the housing and these are connected electrically to the diagnostic electronics. By placing the housing on a region of the body of a patient, the electrodes 2, 3 may be pressed into contact with the skin of the patient and thus the frequency of the heart beat, an electrocardiogram (ECG), the QRS complex of an ECG, may be picked up by the electrodes and, with appropriate pre-amplification, transmitted to the diagnosis electronics. This also applies in the case of an EEG or the like. A voltage source (not shown), in particular a dry battery or a rechargeable accumulator, may also be accommodated in the housing 1, as well as a flat thin graphic display unit 4, preferably a heart beat frequency display unit 5 and an on/off switch 6 connected electrically to the diagnosis electronics. Accordingly, the diagnosis electronics also comprises, on the one hand, evaluation electronics and, on the other hand, activation electronics for the graphic display unit 4 and the heart beat frequency display unit 5 which is likewise present here. As depicted in FIG. 1, the housing 1 is an elongated tubular shape. For adaptation to this shape of the housing 1, the two pick-up electrodes 2, 3 are situated on one long side of the housing 1 close to the front and rear ends respectively and the graphic display unit 4 is located on the long side of the housing opposite to the pick-up electrodes 2, 3. The graphic display unit 4 thus extends along the relevant side of housing 1 over substantially its whole length. This ensures that an optimal location is provided for the graphic display unit and, furthermore, it ensures that the pick-up electrodes 2, 3 are at an adequate distance apart from one another to provide reliable results from the point of view of measurement technique. Lastly, this configuration of the housing 1 and the arrangment of the pick-up electrodes and the graphic display unit 4 is expedient for manipulation, because the display on the graphic display unit 4 is particularly easy to observe. It is quite apparent from FIG. 1 that the housing is in the shape of a pocket fountain pen and the pick-up electrode 3 at one end of the housing 1 is in the form of a conventional type of pocket clip.

The cardiac diagnosis instrument illustrated in FIG. 1 can be handled with almost the same ease as a commonly known pen-light used for inspection and diagnosis and which is carried by most doctors at the present time. It has been found that it is sufficient for the housing to have a length from 100 up to 160 mm, preferably 130 mm, and a diameter- or maximum diameter—from 10 up to 40 mm, preferably 16 mm.

Figure 2:
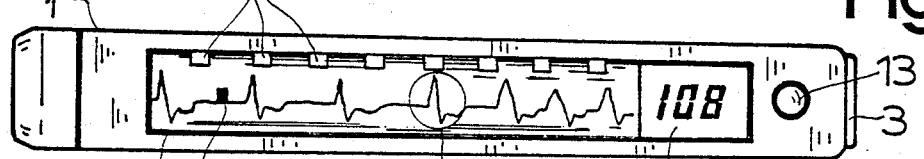
FIG. 2 is an underneath view of the cardiac diagnosis instrument shown in FIG. 1.
Figure 4:
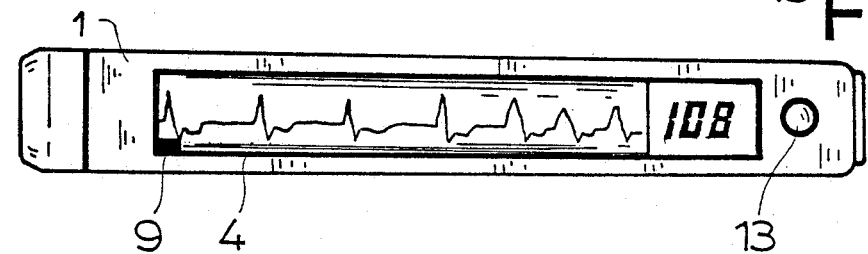
FIG. 4 is an underneath view of a cardiac diagnosis instrument shown in FIG. 3.

The preferred implementation of the graphic display unit 4 is a liquid crystal display (LCD), for example the known LCD-Graphic-Display manufactured by Hitachi Ltd. However, the graphic display unit 4 could be implemented as a flat display screen which is commercially available at the present time, or else it could be built up from a series of flat display screens arranged alongside each other in order to provide the necessary minimum length at least. With regard to the heart beat frequency display unit 5, it is shown in FIG. 2 that this can be an LCD digital display. An LED digital display could also be used, but it has a higher current consumption than the LCD. The positive factor in this case is that the LED display can be seen even in the dark. In any case, it is recommended that the heart beat frequency display unit 5 should be integrated with the graphic display unit 4, as indicated in FIG. 2 and FIG. 4.

Because of the limited dimensions of the graphic display unit 4 of the cardiac diagnosis instrument, it is expedient to be able to adjust the resolution of said graphic display unit 4. Primarily it is possible that the resolution of the graphic display unit 4 may be adjusted by means of a resolution selector switch 8, preferably in the steps of 0.5 mV/cm, 1.0 mV/cm and 3 mV/cm. In FIG. 1, this resolution selector switch 8 with its three positions is shown to be at the 0.5 mV/cm setting. For an EEG examination, the situation is that, with the use of the cardiac diagnosis instrument it is only possible to demonstrate the existence of brain currents, and only if there is appropriate pre-amplification of the input signal (pre-amplification approx. 1000×). A qualitative brain current observation can provide valuable additional information regarding the condition of a patient.

An alternative to the manual adjustment of the resolution of the graphic display unit 4, but in addition thereto, the resolution of the graphic display unit 4 may also be done automatically and preferably in a substantially infinitely-variable (stepless) manner depending upon the maximum amplitude of the heart action. Such automatic tracking of the resolution is readily attainable with modern control engineering without any difficulty (lock-in procedure). This alternative has been implented in the instrument shown in FIG. 3.

If the resolution of the graphic display unit 4 is adjustable, then it is expedient to have a reference display 9, for any selected or given resolution, located in the graphic display unit 4 itself. That does not mean to say that this reference display 9 should be present as a separate unit but, for example in the case of an LCD graphic display, the reference display 9 should appear when there is a specified selection of the graphic display on the graphic display unit 4. Here this reference display 9 is a 1.0 mV-Block in an easily observable position (see FIG. 2 and FIG. 4).

It is apparent from FIG. 2 that the reference display 9 is adjusted to appear on the null line of the ECG or EEG as the case may be. As opposed to this, FIG. 4 clearly shows that the reference display appears in a free zone of the graphic display unit 4, namely in the bottom left-hand corner of the graphic display unit 4. In any case, the reference display 9 allows the absolute magnitude of the peaks in the ECG to be determined quite independently of the manually or automatically selected resolution of the graphic display unit. This allows the doctor making the examination to draw valuable conclusions therefrom.

An important feature in the development of the cardiac diagnosis instrument is the requirement that it should be possible to freeze the display on the graphic display unit 4 or on the heart beat frequency display unit 5 are desired. For retention of an ECG displayed on the graphic display unit 4, a manually operated holding switch 10 can be provided. If the holding switch 10 is actuated, the potential of the graphic display unit 4 remains unaltered. If the doctor then removes the cardiac diagnosis instrument from contact with the body of the patient, it enables the doctor to analyze the ECG, which is dimensionally defined on the graphic display unit 4, more thoroughly in order to arrive at an unambiguous decision. Expediently the holding switch 10 should have a null setting, a holding setting and an erasing setting, as indicated in the example of embodiment depicted in FIG. 1.

Figure 3:
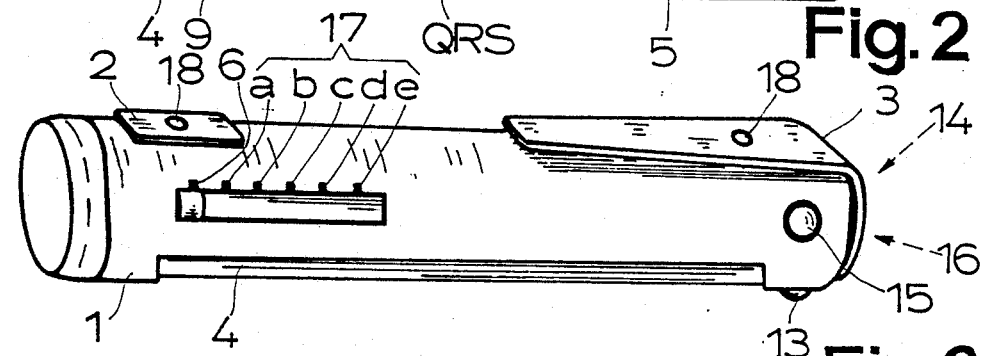
FIG. 3 is a perspective view of a second embodiment of a cardiac diagnosis instrument.

FIG. 3 is an illustration of an example of embodiment in which the holding—or freezing—of an ECG displayed on the graphic display unit 4 is effected automatically, and this is actually done at the time of removal of the pick-up electrodes 2, 3 from contact with the body of the patient once the examination has been completed. When the pick-up electrodes 2, 3 are once again placed in contact with the body of the patient, the retained ECG is erased and a renewed examination can be initiated and proceeded with. It is especially advantageous for the path resistance between the pick-up electrodes 2, 3 to serve as the criterion for initiation of the procedure. Experiments have shown that it is expedient for the path-resistance initiation criterion to be selected so that the ECG will be actively displayed at a path resistance of less than 3 kiloohms and the ECG display will be frozen on the screen when the path resistance is greater than 3 kiloohms.

It is an advantage if the diagnosis electronics is provided with a data storage device so that the ECG displayed on the graphic display unit 4 is able to be stored in said storage device. It is especially recommended that the data storage device should be designed with a storage capacity for several ECG observations. In contrast to the "freezing" of the display which has already been discussed but which only allows for the retention of a single momentary observation, the storage of ECG observations by electronic means allows for the retention of several momentary observations, for example those involved with momentary characteristic alterations of the ECG. In order to be able to determine which of the storage devices is occupied and which is still free, it is possible to make use of storage displays. For this purpose, as indicated in FIG. 2, a storage display 11 with several display stations is provided along the top edge of the graphic display unit 4 and by actuation of this storage display 11 it is possible to determine which of the storage units are already occupied and which are not.

For control of the storage of an ECG which is displayed on the graphic display unit 4, it is sufficient to have a storage command switch 12, as shown in FIG. 1, which is in the form of a push-botton switch. In a similar manner to the freezing of a display on the graphic display unit 4, the electronic storage may be initiated automatically by the removal of the housing 1 with the pick-up electrodes 2, 3 from contact with the body of the patient.

Lastly, it is recommended that the contents of the storage devices in the diagnosis electronics should be recorded as hard copy by means of a strip recorder or a strip printer which can be connected to the cardiac diagnosis instrument. In this way it is possible to obtain a simultaneous or subsequent complete documentation of an emergency case.

Figure 5:
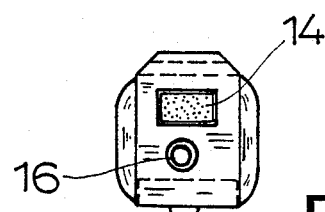
FIG. 5 is an end elevation, seen from the right-hand side, of the cardiac diagnosis instrument shown in FIG. 3.

As shown in FIG. 1, it is possible without any difficulty to incorporate an optical QRS display 13, especially in the form of an LED display, into the housing 1 of the cardiac diagnosis instrument and to connect it to the diagnosis electronics. Correspondingly, there is also the valid possibility of being able to provide an acoustic QRS indicator 14 in the housing 1, especially in the form of a piezo loud speaker, and for this to be connected electrically to the diagnosis electronics. It may be recognized from FIG. 5 that the acoustic QRS indicator 14 is located on the end of housing 1 which is opposite to the end where the examination light 7 is located. The heat beat of a patient may thus be distinctly detected either optically or acoustically. In addition to this, it is also expedient for an optical display or acoustic alarm, especially in the form of a LED-display or a piezo loud speaker, to be provided in the housing 1 and for it to be connected electrically to the diagnosis electronics. According to FIG. 1 and FIG. 3, only an optic alarm display 15 in the form of an LED-display is provided. In the case of a purely acoustic alarm, it is expedient to have it adjusted to be actuated only below a lower limit of 50 heart beats per minute and above an upper limit of 150 heart beats per minute. That should provide a sufficient coverage for most emergencies.

It has previously been pointed out that it could be expedient to connect the cardiac diagnosis instrument to other external instruments, in particular to a strip recorder or the like. For this purpose, and also for the charging of a rechargeable accumulator, it is recommended that an electrical terminal socket 16 should be provided in the housing 1 to receive a plug-in transmission cable or the like. In accordance with FIG. 5, this electrical socket 16 should be located at one end of the housing, in order not to cause any unnecessary "emcumbrance" along the side of the housing, especially in the case of the elongated tubular configuration depicted in the drawings of examples of embodiment of the invention. Furthermore, a transmission cable running from the socket 16 in the axial direction of the instrument is much more convenient to manipulate than a cable projecting radially from the side of the instrument.

As shown clearly in FIG. 1 and FIG. 3, apart from an on-off switch 6, there is also a function-selector switch 17 provided for selection of the various possible functions of the cardiac diagnosis instrument. A special feature of both the examples of embodiment depicted is the fact that the on-off switch 6 and the function-selector switch 17 are integrated into a multistage switch. A multistage switch could be configured as a rotary switch but, because of the preferred elongated tubular shape of the cardiac diagnosis instrument housing 1, it is preferred to have the requisite switches 6, 8, 10, 17 implemented as sliding switches arranged in the longitudinal direction of the housing 1 as shown in FIG. 1 and FIG. 3.

The embodiment of a completely-outfitted cardiac diagnosis instrument illustrated in FIG. 1 possesses, along with the on-off switch, the integrated function-selector switch 17 with settings for the examination light, ECG optical QRS, ECG acoustic QRS, ECG graphic display, EEG graphic display (1000×amplification). Furthermore, it may be recognized from FIG. 1 that the holding switch 10 is integrated with the on-off switch 6 and the function-selector switch 17.

In contrast, the cardiac diagnosis instrument shown in FIG. 3 is only provided with the on-off switch 6 integrated with the function-selector switch 17. Because no facility for data storage is provided here, there is naturally no switch for initiation and erasure of storage. There is also no resolution selection switch provided because the resolution is controlled automatically. Lastly, this instrument does not include an examination light.

It is a common feature of both embodiments that the pick-up electrodes 2, 3 are provided with connector elements for coupling by jack plug with continuously-operating, or long-time, electrodes. In the illustrated examples of embodiments, these connector elements are in the form of socket openings 18 into which jack plugs, connected to the usual type of continuously-operating electrodes, with substantially spherical plug-in heads, such as are commercially available, may be inserted. This measure makes it possible to use the cardiac diagnosis instrument not only for short-term emergency observations, but also for longer-term monitoring of a patient's heart condition. Especially in combination with an electrical terminal connection 16 for a transmission cable, it is possible to employ the cardiac diagnosis instrument as a stationary item of equipment in a hospital, quite apart from its use as a mobile instrument for dealing with emergencies.

It has already been stated that the previously discussed preferred embodiments of the cardiac diagnosis instrument are such that they can be handled with the same ease as the known type of examination pen-light used by doctors. As shown in FIG. 1, it is also possible to combine the cardiac diagnosis instrument with an examination light, that is to say an examination light 7 may be included at one end of the housing 1. On the one hand, this combination of the cardiac diagnosis instrument with an examination pen-light has the advantage that one and the same instrument may be used as two quite essential aids by the doctor in emergencies and on the other hand, the illumination power of the pen-light 7 may be used as an indication as to whether or not the voltage source, namely the battery or accumulator, is still adequately charged.

The claims defining the invention are as follows:

1. Cardiac diagnosis instrument including an elongated housing, diagnosis electronics accommodated within the housing and two pick-up electrodes mounted on one long side of the housing close to the front and rear ends of the instrument and electrically connected to the diagnosis electronics, a voltage source within the housing, a flat thin graphic display unit which extends along one side for a substantial part of the length of the housing on the opposite side so that on which the pick-up electrodes are located, on on-off switch, said graphic display unit and said on-off switch being electrically connected to the diagnosis electronics, said diagnosis electronics including evaluation electronics and actuation electronics for the graphic display unit, said housing having a tubular shape somewhat like that of a fountain pen, and by placing the housing on a region of the body of a patient, the pick-up electrodes may be pressed into contact with the skin of the patient and thus the frequency of the heart beat, an electrocardiogram (ECG), and the QRS complex of an ECG may be investigated through the medium of the pick-up electrodes, and wherein one of the pick-up electrodes is in the form of a holding clip starting from one end of the housing.

2. Cardiac diagnosis instrument in accordance with claim 1, wherein the housing has a length from 100 up to 160 mm, preferably 130 mm, and a diameter—or maximum diameter—from 10 up to 40 mm, preferably 16 mm.

3. Cardiac diagnosis instrument in accordance with claim 1, wherein the resolution of the graphic display unit is adjusted automatically depending upon the maximum amplitude of the heart action.

4. Cardiac diagnosis instrument in accordance with claim 3, wherein there is a reference display, preferably a 1.0 mV-Block, corresponding to a selected or given resolution, provided in the graphic display unit.

5. Cardiac diagnosis instrument in accordance with claim 1, wherein an ECG displayed on the graphic display unit may be selectively retained (freezing of the display), wherein the freezing of the display is effected automatically at the actual time when the pick-up electrodes are removed from contact with the skin of a patient after completion of an observation.

6. Cardiac diagnosis instrument in accordance with claim 5, wherein the replacement of the pick-up electrodes on the skin causes erasure of the retained ECG and initiates the continuation of the observation procedure.

7. Cardiac diagnosis instrument in accordance with claim 6, wherein the path resistance between the pick-up electrodes serves as the criterion for initiation of the procedure so that, in particular, the ECG will be actively displayed at a path resistance of less than 3 kiloohms and the ECG display will be frozen on the screen when the path resistance is greater than 3 kiloohms.

8. Cardiac diagnosis instrument in accordance with claim 7, wherein the path resistance between the pick-up electrodes serves as the criterion for initiation of the procedure so that, in particular, the ECG will be actively displayed at a path resistance of less than 3 kiloohms and the ECG display will be frozen on the screen when the path resistance is greater than 3 kiloohms.

9. Cardiac diagnosis instrument in accordance with claim 1, wherein the on-off switch and any other desired switches are implemented as a sliding switch which is arranged or attached in the longitudinal direction of the housing.

10. Cardiac diagnosis instrument in accordance with claim 1, wherein an examination pen-light is provided at one end of the housing.

11. Cardiac diagnosis instrument including an elongated housing diagnosis electronics accommodated within the housing and two pick-up electrodes mounted on the housing close to the front and rear ends of the instrument and electrically connected to the diagnosis electronics, a voltage source within the housing, a flat thin graphic display unit which extends along one side of the housing, an on-off switch, said graphic display unit and said on-off switch being electrically connected to the diagnosis electronics, said diagnosis electronics including evaluation electronics and actuation electronics for the graphic display unit, said housing having a tubular shape somewhat like that of a fountain pen, and by placing the housing on a region of the body of a patient, the pick-up electrodes may be pressed into contact with the skin of the patient for enabling electrically monitorable physical conditions of the patient to be investigated through the medium of the pick-up electrodes, and wherein an examination pen-light is provided at one end of the housing.

* * * * *